US006454999B1

(12) United States Patent
Farhangnia et al.

(10) Patent No.: US 6,454,999 B1
(45) Date of Patent: Sep. 24, 2002

(54) INTEGRATED BLOOD PUMP AND OXYGENATOR SYSTEM HAVING EXTENDED BLOOD FLOW PATH

(75) Inventors: Mehrdad Farhangnia, Sunnyvale, CA (US); Alex Leynov, Walnut Creek, CA (US); Joseph Loeffler, Mountain View, CA (US); Alec A. Piplani, Mountain View, CA (US); Greg Potts, Mountain View, CA (US); Christian Skieller, Redwood City, CA (US)

(73) Assignee: Cardiovention, Inc., Santa Clara, CA (US)

( * ) Notice: Subject to any disclaimer, the term of this patent is extended or adjusted under 35 U.S.C. 154(b) by 0 days.

(21) Appl. No.: 09/430,244

(22) Filed: Oct. 29, 1999

Related U.S. Application Data

(63) Continuation-in-part of application No. 09/223,676, filed on Dec. 30, 1998, now Pat. No. 6,379,618.

(51) Int. Cl.[7] .......................... A61M 1/14; A61M 1/34; A61M 37/00; B01D 47/00
(52) U.S. Cl. ...................... 422/45; 422/48; 604/6.11; 604/6.14; 96/257; 261/DIG. 28
(58) Field of Search ................ 422/44–48; 604/4.01, 604/6.09, 6.11, 6.13, 6.14; 96/4, 7–11, 243, 267–269, 303–305, 355–361; 210/321.81, 321.9, 321.72, 321.78, 321.87, 500.23, 348, 456, 257, 295, 433.1; 261/DIG. 28

(56) References Cited

U.S. PATENT DOCUMENTS

| 3,026,871 | A | 3/1962 | Thomas | 128/214 |
| 3,204,631 | A | 9/1965 | Fields | 128/214 |
| 3,466,148 | A | 9/1969 | Everett | 23/258.5 |

(List continued on next page.)

FOREIGN PATENT DOCUMENTS

| AU | 564831 | 8/1987 | A61M/1/00 |
| EP | 0 599 138 A2 | 1/1994 | A61M/1/10 |
| GB | 1 437 493 | 9/1973 | A61M/1/03 |

OTHER PUBLICATIONS

Berman, J. et al., "Transport in Rotating Tubular Oxygenators," Biomedical Engineering Center, Northwestern University, 4 pgs.

Berman, J. et al., "Mass Transfer to Fluids Flowing Through Rotating Nonaligned Straight Tubes," *Journal of Biomedical Engineering*, R. Skalek et al., eds., The American Society of Mechanical Engineers, 1986, pp. 342–349.

Gaylor, J.D.S. et al., "Gas Transfer and Thrombogenesis in an Annular Membrane Oxygenator with Active Blood Mixing," *Transactions: American Society for Artificial Internal Organs, vol. XIX*, G.E. Schreiner et al., eds., Georgetown University Printing Department, 1973, pp. 516–524.

(List continued on next page.)

*Primary Examiner*—Angela D. Sykes
*Assistant Examiner*—P M Bianco
(74) *Attorney, Agent, or Firm*—Fish & Neave; Nicola A. Pisano (57) ABSTRACT

An integrated blood pump/oxygenator having a rotating hollow fiber bundle assembly that both oxygenates and pumps blood is provided that includes a plurality of partitions disposed within or about the fiber bundle assembly to lengthen the flow path of blood passing through the fiber bundle. Alternatively, or in addition, blood flow paths may be lengthened and oxygenation improved by providing internal recirculation paths within the pump/oxygenator, which also advantageously may be used to reduce blood trauma caused by stagnation nearing moving parts and heat build-up.

24 Claims, 5 Drawing Sheets

U.S. PATENT DOCUMENTS

| | | | |
|---|---|---|---|
| 3,468,631 A | 9/1969 | Raible et al. | 23/258.5 |
| 3,674,440 A | 7/1972 | Kitrilakis | 23/258.5 |
| 3,768,977 A | 10/1973 | Brumfield et al. | 23/258.5 |
| 3,794,468 A | 2/1974 | Leonard | 23/258.5 |
| 3,841,837 A | 10/1974 | Kitrilakis et al. | 23/258.5 |
| 3,970,408 A | 7/1976 | Rafferty et al. | 415/60 |
| 3,998,593 A | 12/1976 | Yoshida et al. | 23/258.5 |
| 4,075,091 A | 2/1978 | Bellhouse | 210/19 |
| 4,220,535 A | 9/1980 | Leonard | 210/321 |
| 4,376,095 A | 3/1983 | Hasegawa | 422/46 |
| 4,400,275 A | 8/1983 | Ramshaw et al. | 210/321.1 |
| 4,490,331 A | 12/1984 | Steg, Jr. | 422/46 |
| 4,558,996 A | 12/1985 | Becker et al. | 417/374 |
| 4,620,965 A | 11/1986 | Fukusawa et al. | 422/46 |
| 4,639,353 A * | 1/1987 | Takemura et al. | 128/DIG. 3 |
| 4,698,207 A | 12/1987 | Bringham et al. | 422/46 |
| 4,791,054 A | 12/1988 | Hamada et al. | 435/2 |
| 4,808,378 A | 2/1989 | Nakanishi et al. | 422/48 |
| 4,944,748 A | 7/1990 | Bramm et al. | 623/3 |
| 4,975,247 A | 12/1990 | Badolato et al. | 422/48 |
| 5,049,134 A | 9/1991 | Golding et al. | 604/151 |
| 5,059,374 A * | 10/1991 | Krueger et al. | 210/321.61 |
| 5,162,101 A | 11/1992 | Cosentino et al. | 422/46 |
| 5,169,530 A | 12/1992 | Schucker et al. | 210/321.81 |
| 5,217,689 A | 6/1993 | Raible | 422/46 |
| 5,230,862 A | 7/1993 | Berry et al. | 422/48 |
| 5,263,924 A | 11/1993 | Mathewson | 604/4 |
| 5,266,265 A | 11/1993 | Raible | 422/46 |
| 5,270,005 A | 12/1993 | Raible | 422/46 |
| 5,271,743 A | 12/1993 | Hattler | 604/26 |
| 5,308,314 A | 5/1994 | Fukui et al. | 604/4 |
| 5,308,320 A | 5/1994 | Safer et al. | 604/4 |
| 5,312,589 A | 5/1994 | Reeder et al. | 422/45 |
| 5,352,361 A | 10/1994 | Prasad et al. | 210/321.81 |
| 5,391,142 A | 2/1995 | Sites et al. | 604/4 |
| 5,399,074 A | 3/1995 | Nose et al. | 417/423.1 |
| 5,411,706 A | 5/1995 | Hubbard et al. | 422/46 |
| 5,575,630 A | 11/1996 | Nakazawa et al. | 417/420 |
| 5,591,404 A | 1/1997 | Mathewson | 422/48 |
| 5,601,418 A | 2/1997 | Ohara et al. | 417/420 |
| 5,626,759 A | 5/1997 | Krantz et al. | 210/645 |
| 5,626,819 A | 5/1997 | Novello et al. | 422/45 |
| 5,643,794 A | 7/1997 | Liu et al. | 435/289.1 |
| 5,728,069 A | 3/1998 | Montevecchi et al. | 604/151 |
| 5,770,149 A | 6/1998 | Raible | 422/46 |
| 5,830,370 A | 11/1998 | Maloney et al. | 210/780 |
| 5,900,142 A * | 5/1999 | Maloney et al. | 210/179 |
| 6,106,776 A * | 8/2000 | Borovetz et al. | |

OTHER PUBLICATIONS

Gaylor, J.D.S. et al., "The Taylor–Vortex membrane oxygenator: design analysis based on a predictive correlation for oxygen transfer," *Physiological and Clinical Aspects of Oxygenator Design,* S.G. Dawids & H.C. Engell, eds., Elsevier Scientific Publishing Co., 1976, pp. 65–76.

Illickal, M.M. et al., "Boundary Layer Phenomenon in Membrane Oxygenators," *Surgical Forum,* H.W. Scott et al., eds., American College of Surgeons, 1968, pp. 134–136.

Kitrilakis, S. et al., "A Rotating Disk Membrane Oxygenator," *Artificial Lungs for Acute Respiratory Failure, Theory and Practice,* W. Zapol and J. Qvist eds., Academic Press, 211–221 (1976).

Lewis, F.R. et al., "A Combined Membrane Pump–Oxygenator: Design and Testing," *Transactions: American Society for Artificial Internal Organs, vol. XX–A,* G.E. Schreiner et al., eds., Georgetown University Printing Department, 1974, pp. 253–261.

Makarewicz, A.J. et al. "A Pumping Intravascular Artificial Lung with Active Mixing," *ASAIO Journal,* 39(3): M466–M469 (1993).

Makarewicz, A.J. et al., "A Pumping Intravascular Artificial Lung with Active Mixing," *ASAIO Journal,* 40(3): M518–M521 (1994).

Makarewicz, A.J. et al., "New Design for a Pumping Artificial Lung," *ASAIO Journal,* 42(5):M615–M619 (1996).

Mottaghy, K. et al., "Effect of Combined Shear, Secondary and Axial Flow of Blood on Oxygen Uptake," *Chem. Eng. Commun.: vol. 36,* Gordon and Breach Science Publishers, 1985, pp. 269–279.

Ratan, Ram S. et al., "Experimental evaluation of a rotating membrane oxygenator," *The Journal of Thoracic and Cardiovascular Surgery: vol. 53, No. 4,* B. Blades, ed., The C.V. Mosby Co., 1967, pp. 519–526.

Sakakibara, Shigeru et al., "The Centrifugal Oxygenator: Clinical Experience in 1,215 Patients," *The Annals of Thoracic Surgery: vol. 6, No. 5,* 1968, pp. 443–449.

Smeby, L.C., "The Taylor–Vortex Membrane Oxygenator," *Artificial Organs,* R.M. Kenedi et al., eds., University Park Press, 1977, pp. 70–82.

Subramanian, V.A. et al., "Comparative Evaluation of a New Disposable Rotating Membrane Oxygenator with Bubble Oxygenator," *The Annals of Thoracic Surgery: vol. 21, No. 1,* Little, Brown, and Co., 1976, pp. 48–54.

* cited by examiner

INTEGRATED BLOOD PUMP AND OXYGENATOR SYSTEM HAVING EXTENDED BLOOD FLOW PATH

REFERENCE TO RELATED APPLICATIONS

This application is a continuation-in-part of U.S. patent application Ser. No. 09/223,676, filed Dec. 30, 1998, now U.S. Pat. No. 6,379,618.

Field of the Invention

The present invention relates to extracorporeal systems for oxygenating and pumping blood during cardiac surgery. More specifically, the present invention relates to an integrated oxygenator and pump system having a rotating annular fiber bundle including flow-path lengthening baffles and internal recirculation paths.

BACKGROUND OF THE INVENTION

Each year hundreds of thousands of people are afflicted with vascular diseases such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

Recently, the development of minimally invasive techniques for cardiac bypass grafting, for example, by Heartport, Inc., Redwood City, Calif., and CardioThoracic Systems, Inc., Cupertino, Calif., have placed a premium on reducing the size of equipment employed in the sterile field. Whereas open surgical techniques typically provide a relatively large surgical site that the surgeon views directly, minimally invasive techniques require the placement of endoscopes, video monitors, and various positioning systems for the instruments. These devices crowd the sterile field and can limit the surgeon's ability to maneuver.

At the same time, however, the need to reduce priming volume of the oxygenator and pump, and the desire to reduce blood contact with non-native surfaces has increased interest in locating the oxygenator and pump as near as possible to the patient.

In recognition of the foregoing issues, some previously known cardiopulmonary systems have attempted to miniaturize and integrate certain components of cardiopulmonary systems. U.S. Pat. Nos. 5,266,265 and 5,270,005, both to Raible, describe an extracorporeal blood oxygenation system having an integrated blood reservoir, an oxygenator formed from a static array of hollow fibers, a heat exchanger, a pump and a pump motor that is controlled by cable connected to a control console.

The systems described in the foregoing patents employ relatively short flow paths that may lead to inadequate gas exchange, due to the development of laminar flow zones adjacent to the hollow fibers. U.S. Pat. No. 5,411,706 to Hubbard et al. describes one solution providing a longer flow path by recirculating blood through the fiber bundle at a higher flow rate than the rate at which blood is delivered to the patient. U.S. Pat. No. 3,674,440 to Kitrilakis and U.S. Pat. No. 3,841,837 to Kitrilakis et al. describe oxygenators wherein the gas transfer surfaces form an active element that stirs the blood to prevent the buildup of boundary layers around the gas transfer surfaces.

Makarewicz et al., "New Design for a Pumping Artificial Lung," *ASAIO Journal*, 42(5):M615–M619 (1996), describes an integrated pump/oxygenator having a hollow fiber bundle that is potted between an inlet gas manifold and an outlet gas manifold. The fiber bundle is rotated at high speed to provide pumping action, while oxygen flowing through the fiber bundle oxygenates the blood.

U.S. Pat. No. 5,830,370 to Maloney et al. describes a device having a fiber bundle mounted for rotation between a fixed central diffuser element and an outer wall of a housing. The fiber bundle is rotated at speeds sufficiently high to cause shear forces that induce turbulent flow within the blood. Within the fiber bundle, blood flows radially outward due to centrifugal force, and may have an insufficient residence time to provide adequate mass transfer at high bundle angular velocities.

Although the devices having rotating fiber bundles described in the foregoing references offer some desirable features, such as low priming volume and low surface area, it is unclear whether such devices can provide commercially desirable levels of oxygenation over a wide range of flow rates. In addition, such previously known devices may be subject to creation of stagnation and heat-buildup zones, such as near bearing surfaces.

Other patents have addressed the problem of reducing boundary layer impedance to mass and heat transfer in a stationary hollow fiber bundle by promoting radial cross-flow within the fiber bundle. For example, U.S. Pat. No. 5,352,361 to Prasad et al. describes a stationary fiber bundle having a plurality of axially symmetric baffles disposed along the shell side of a tube and shell heat/mass exchange system to promote radial cross-flow through the bundle. U.S. Pat. No. 5,169,530 to Schucker et al. describes a hollow fiber bundle having a plurality of radially disposed fluid impermeable baffles that divide the bundle into discrete sub-bundles. U.S. Pat. No. 4,220,535 to Leonard describes a tube and shell hollow fiber permeator having a partition in the shell portion of the bundle that enhances flow uniformity radial cross-flow in the resulting bundle zones.

While the foregoing patents describe the use of baffles to promote cross-flow in stationary fiber bundles, such baffling arrangements are uniformly absent in previously known rotating fiber bundle designs, where rotation of the fiber bundle itself provides adequate cross-flow through the fiber bundle.

In view of the foregoing, it would be desirable to provide an integrated blood oxygenator and pump having a rotating fiber bundle that provides compact size, low priming volume, low surface area and adequate oxygenation over a wide range of bundle angular velocities.

It also would be desirable to provide an integrated blood oxygenator and pump having a rotating fiber bundle, wherein the blood follows a tortuous path of increased length while flowing through the bundle, compared to having the blood pass outward along a radius of the bundle.

It further would be desirable to provide an integrated blood oxygenator and pump having a rotating fiber bundle, wherein a recirculation flow is provided near critical areas of the device to avoid heat build-up and stagnation.

It still further would be desirable to provide an integrated blood oxygenator and pump having a rotating fiber bundle and inter-bundle baffles that provide increased oxygen transfer compared to previously known rotating bundle designs.

SUMMARY OF THE INVENTION

In view of the foregoing, it is an object of the present invention to provide an integrated extracorporeal blood pump/oxygenator having a compact size, low priming volume and the ability to adequately oxygenate blood using a rotating fiber bundle that reduces boundary layer resistance to gas transfer and the formation of stagnation zones within the fiber bundle.

It is another object of the present invention to provide an integrated blood oxygenator and pump having a rotating fiber bundle, wherein the blood follows a tortuous path of increased length while flowing through the bundle, compared to having the blood pass outward along a radius of the bundle.

It is a further object of this invention to provide an integrated blood oxygenator and pump having a rotating fiber bundle, wherein a recirculation flow is provided near critical areas of the device to avoid heat build-up and stagnation.

It is yet another object of this invention to provide an integrated blood oxygenator and pump having a rotating fiber bundle and a plurality of baffles disposed within the bundle that provide increased oxygenation compared to previously known rotating bundle designs.

These and other objects of the invention are accomplished by providing an integrated blood pump/oxygenator, suitable for use within a sterile field, that has a low priming volume. In accordance with the principles of the present invention, the pump/oxygenator includes a rotating hollow fiber bundle assembly that both oxygenates the blood and develops additional pressure head, if desired, to pump the blood. The device further includes either (i) baffles for lengthening the flow path for blood passing through the fiber bundle and enhancing the oxygen transfer within the fiber bundle or (ii) means for recirculating blood to avoid the creation of stagnation or heat build-up zones.

In a preferred embodiment, the integrated blood pump/oxygenator of the present invention comprises an annular fiber bundle mounted for rotation within a housing, wherein deoxygenated blood is introduced into a central void of the bundle and passes outward through the bundle by centrifugal force. In accordance with the present invention, the annular bundle includes at one or more radial locations a plurality of baffles that extend over an arc of the circumference and that deflect the blood from following a straight-radially outward path. In addition, such baffles may have a radial dimension.

In accordance with another aspect of the present invention, appropriately sized gaps or pathways may be provided between the rotating annular fiber bundle and the housing to reduce the creation of heat-buildup or stagnation zones within the blood and to enhance recirculation and wash-out, thereby reducing the risk of blood trauma and platelet activation.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides an integrated blood oxygenator and pump that combines active blood oxygenation using a rotating fiber bundle with baffles that increase oxygenation of blood passing through the fiber bundle and also may generate additional pressure head, thereby overcoming the drawbacks of previously known devices. In accordance with the principles of the present invention, the device may be placed in or near the sterile field and preferably has a low priming volume, e.g., 250 cc or less. In addition, the device of the present invention may include internal recirculation paths that enhance wash-out of potential stagnation and heat build-up zones, thereby reducing the risk of blood trauma.

Figure 1:
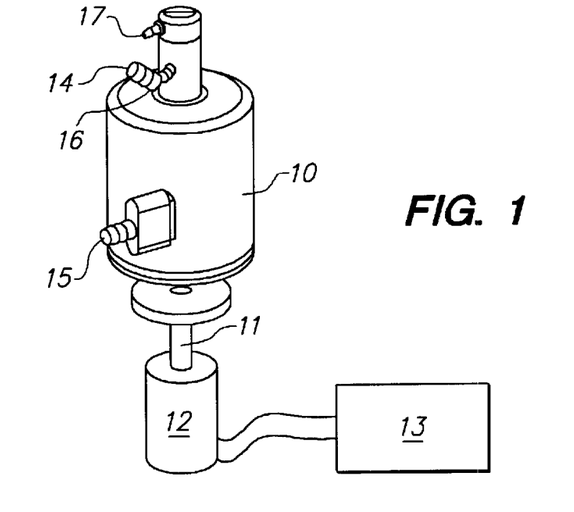
FIG. 1 is a perspective view of an integrated blood oxygenator and pump system suitable for implementing the present invention.
Figure 2A:
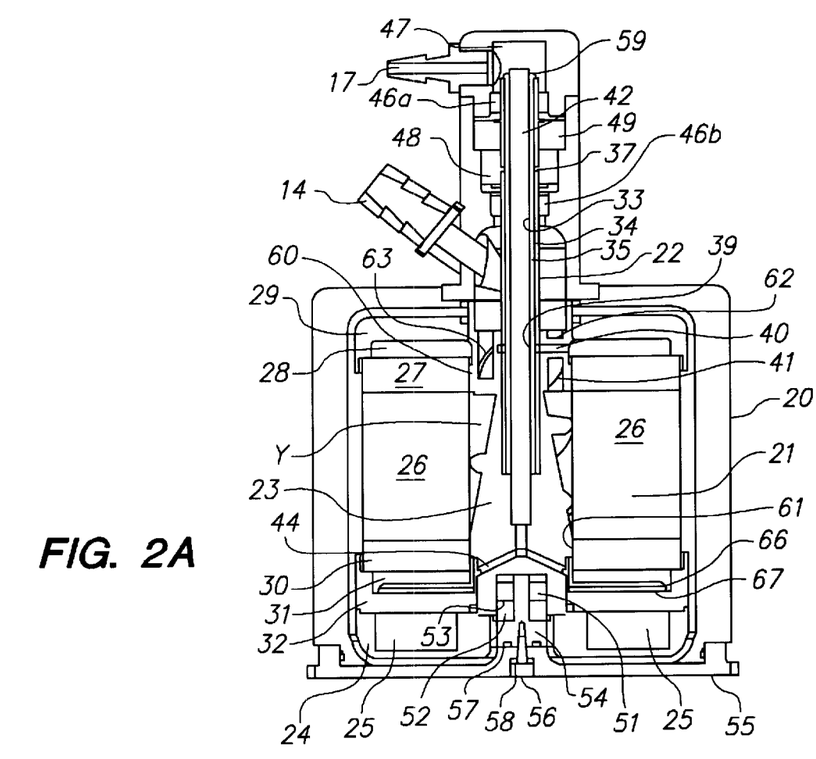
FIGS. 2A and 2B are, respectively, side-sectional and cut-away views of the device of FIG. 1.
Figure 2B:
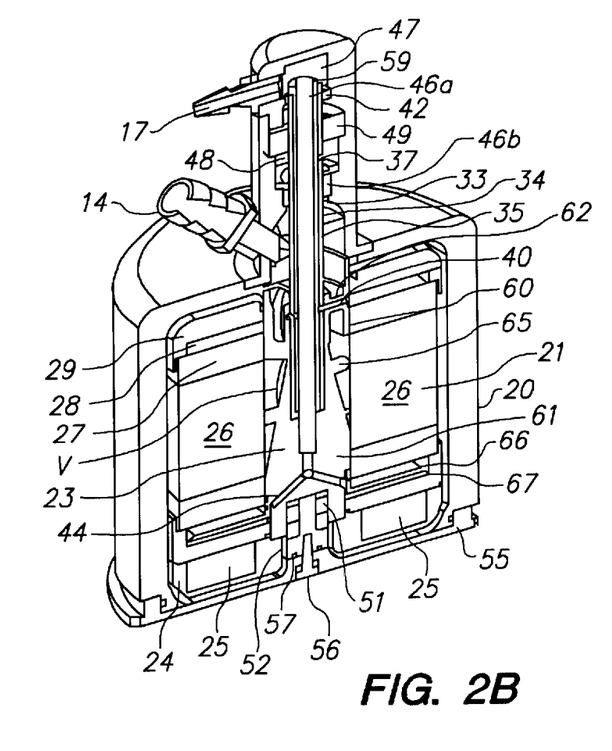

Referring to FIGS. 1, 2A and 2B, an integrated blood pump/oxygenator 10 suitable for implementing a device in accordance with the principles of the present invention is described. Pump/oxygenator 10 is of the type described in co-pending, commonly assigned U.S. patent application Ser. No. 09/223,676, filed Dec. 30, 1998, which is incorporated herein by reference, and includes several improvements over the previously known rotating fiber bundle designs.

Pump/oxygenator 10 is magnetically coupled to drive shaft 11 of motor 12, which is in turn controlled by controller 13. Deoxygenated venous blood is supplied to pump/oxygenator 10 via suitable biocompatible tubing (not shown) coupled to venous blood inlet 14; oxygenated blood passes out of pump/oxygenator 10 through blood outlet 15. Pressurized oxygen is introduced into pump/oxygenator 10 via gas inlet port 16, while a mixture of oxygen and carbon dioxide exits pump/oxygenator 10 via gas outlet port 17.

Motor 12, magnetically coupled drive shaft 11 and controller 13 are items per se known in the art, and may comprise any of a number of systems available from Bio-Medicus, Inc., Eden Prairie, Minnesota. Alternatively, drive shaft 11, motor 12 and controller 13 may be miniaturized to permit their placement closer to the patient.

Referring now to FIGS. 2A and 2B, pump/oxygenator 10 comprises housing 20 enclosing fiber bundle assembly 21 that rotates within housing 20 on shaft 22. Shaft 22 is affixed to shaft impeller 23, which is attached to tray 24. Tray 24 holds magnets 25 that are used to magnetically couple fiber bundle assembly 21 to drive shaft 11.

Fiber bundle 26 preferably comprises a multiplicity of microporous hollow fiber elements having an upper end potted in region 27, so that the interior lumens of the fibers communicate with plenum 28 in inlet gas manifold 29.

Likewise, the lower ends of the hollow fiber elements of fiber bundle 26 are potted in region 30, so that the interior lumens of the fibers communicate with plenum 31 in outlet gas manifold 32. Any of a number of suitable biocompatible potting materials may be used, such as polyurethanes or epoxies.

Shaft 22 includes inner tube 33 and outer tube 34 arranged coaxially to form annulus 35. Annulus 35 communicates with gas inlet port 16 (see FIG. 1) via through-wall holes 37, and with plenum 28 of inlet gas manifold 29 via through-wall holes 39 and passageways 40 in plurality of pumping vanes 41. Lumen 42 of inner tube 33 communicates with gas outlet port 17 at its upper end and plenum 31 in outlet gas manifold 32 at its lower end via passageways 44 in shaft impeller 23. Shaft seal 46a separates space 47, which couples gas outlet port 17 to lumen 42, from space 48, which couples gas inlet port 16 (see FIG. 1) to annulus 35. Shaft seal 46b separates space 48 from the interior of housing 20, which encloses fiber bundle assembly 21.

Shaft 22 is carried in bearing 49, while shaft impeller 23 is carried on bearings 51 and 52. Spacer 53 is interposed between bearings 51 and 52, and the entire assembly is in turn carried on bearing shaft 54. Bearing shaft 54 is affixed to lower plate 55 of housing 20 by shoulder screw 56, and is seated on O-ring seal 57. Shoulder screw 56 also is sealed with O-ring 58. Shaft impeller 23 seals the lower end of annulus 35, while the upper end of the annulus is sealed by plug 59.

Shaft impeller 23 (see FIG. 2B) has upper hub 60 and lower hub 61. Upper hub 60 is connected to upper potting 27 and lower hub 61 is connected to lower potting 30. Pumping vanes 62 extend between annulus 35 and upper hub 60, and openings 63 between the plurality of vanes 62 permit blood entering pump/oxygenator 10 via venous blood inlet 14 to flow into void V at the center of the fiber bundle 26. Vanes 62 are configured to serve as vanes that pump and accelerate blood before it passes through the fiber bundle 26. Optionally, shaft impeller 23 may include helical vanes 65 between upper hub 60 and lower hub 61 that further accelerate blood entering void V and urge the blood outward into fiber bundle 26.

Baffle plate 66 is disposed in plenum 31, and includes grooves 67 on its underside that communicate with passageways 44. Baffle plate 66 thus causes gas exiting fiber bundle 26 to pass around the outermost edge of the baffle plate. Accordingly, blood leaking into plenum 31 of outlet gas manifold 32 is cleared from the manifold and entrained in the exhaust gas stream passing through gas outlet port 17.

Figure 3:
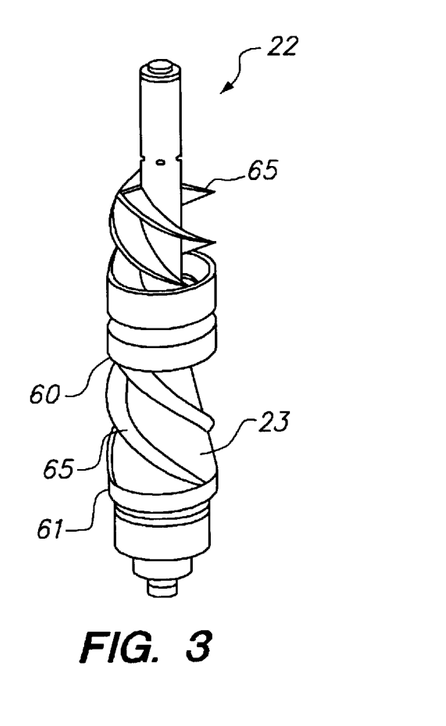
FIG. 3 is a partial view of alternative embodiment of a central shaft suitable for use in the device of FIG. 1.

FIG. 3 shows an alternative embodiment of shaft impeller 23, where helical vanes 65 extend above hub 60 to further augment the pump head developed by rotation of shaft impeller 23 and fiber bundle 26. As will of course be appreciated, the pump housing and seal locations must be appropriately modified to accommodate extended vanes 65 of FIG. 3.

As described in the above-incorporated application, the construction of pump/oxygenator 30 includes a number of advantageous features relative to previously-known rotating fiber bundle systems, including reduced microbubble generation, reduced shear-induced blood trauma, reduced flooding associated with fiber breakage, and reduced stress-induced failure of fibers. Further descriptions of those advantages may be found in the above-incorporated application.

Figure 4:
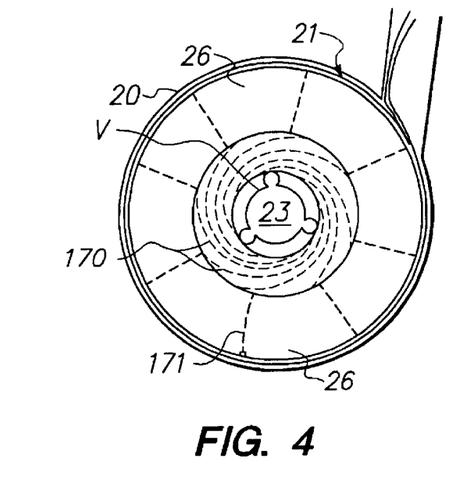
FIG. 4 is a cross-sectional view of the device of FIGS. 1 and 2 depicting blood flow within the device.

Referring now to FIG. 4, movement of blood flowing through the fiber bundle of the device of FIGS. 1 and 2 is described with respect to one aspect of the present invention. In FIG. 4, the individual hollow fibers are omitted for clarity. During operation of the integrated pump/oxygenator of FIGS. 1 and 2, blood entering void V impinges upon impeller shaft 23 and follows spiral path 170 (shown in dotted line) as it gradually accelerates to the angular velocity of fiber bundle 26. Once the blood has reached the angular velocity of the fiber bundle, it enters the fiber bundle and is subjected to centrifugal force ($F=\omega^2 rm$) that causes the blood to follow an essentially radial flow path 171 (shown in dotted line) through the fiber bundle, when viewed from the perspective of an observer moving with the fiber bundle assembly. At the higher rotational speeds that may be required to achieve higher blood flow rates and pumping head from the device, the path for the blood to radially traverse fiber bundle 26 may become too short to achieve effective oxygenation. Accordingly, one aspect of the present invention is directed to lengthening the blood flow path for blood passing through fiber bundle assembly 21, thereby increasing oxygenation.

Figure 5A:
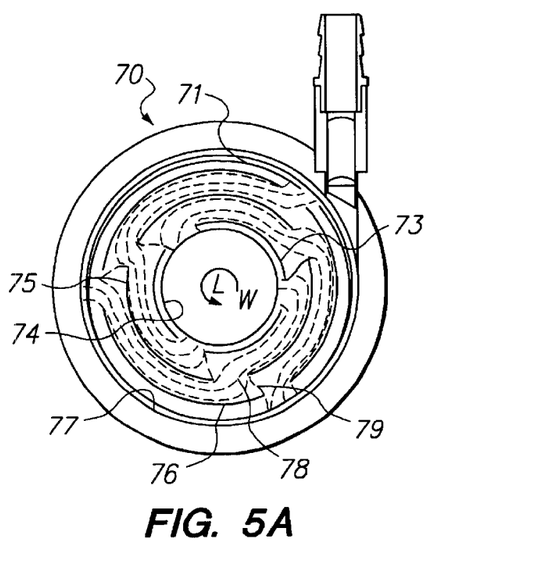
FIGS. 5A–5C are cross-sectional views of devices constructed in accordance with the principles of the present invention.
Figures 5B, 5C:
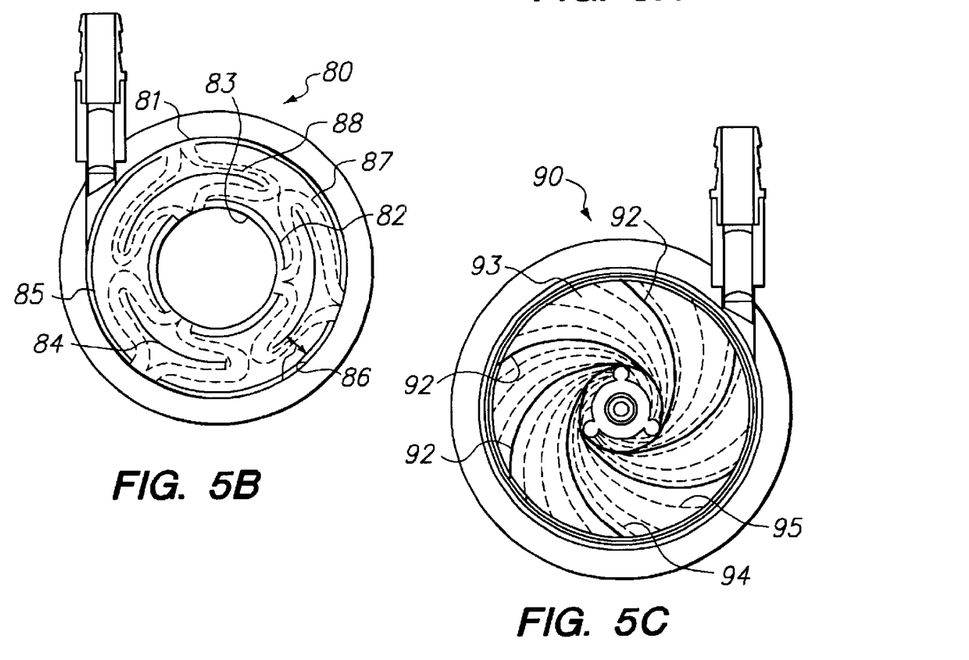

Referring to FIGS. 5A–5C, a number of structures for lengthening the path of blood passing through a rotating fiber bundle are described. In particular, a plurality of circumferentially-disposed fluid impermeable baffles are provided that are disposed on the inner and/or outer surfaces of, or within, the fiber bundle assembly, and re-direct blood flow within the fiber bundle. Baffles configured in accordance with the principles of the present invention force blood to follow a longer path through the fiber bundle and expose the blood to more fibers. The baffles also increase secondary flow around the individual fibers within the fiber bundle, reducing boundary layer resistance. If the baffles further include a radial component, the baffles may be used to partition the fiber bundle into sub-bundles and optionally may serve as vanes that enhance oxygenation.

Figure 6A:
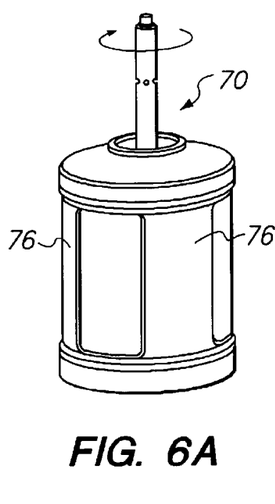
FIGS. 6A–6C are perspective views of fiber bundle assemblies of further alternative embodiments of present invention.

Referring now to FIG. 5A, integrated pump/oxygenator 70 of the present invention is described. Pump/oxygenator 70 preferably is similar in construction to the device of FIGS. 1 and 2, except that fiber bundle assembly 71 includes three sets of off-set, concentric, fluid impermeable baffles: inner baffles 73 disposed on interior surface 74, middle baffles 75 disposed within the fiber bundle assembly 71 and outer baffles 76 disposed on exterior surface 77. Baffles 73, 75, & 76 extend over predetermined arcs of the circumference of the fiber bundle assembly and for the height of the bundle, as depicted in FIG. 6A. Illustratively, the baffles are spaced equidistant apart from one other within each set, and each set is spaced equidistant apart from the next set. Different spacing and/or number of baffles may be employed. Representative expected flow paths 78 and 79 for blood passing through the fiber bundle assembly are shown in dotted line in FIG. 5A.

In particular, based on the packing density of the porous fibers of bundle assembly 71, middle baffles 75 may be shifted to lengthen the flow path of the blood, illustratively shown by paths 78 and 79. Viscous forces within the blood retard flow between the baffles. In the reference frame ω of the rotating fiber bundle, blood prefers to flow in the opposite direction as ω (i.e. clockwise). Thus, baffles 75 are also shifted in the clockwise direction to increase the length of the blood flow path through the bundle.

In FIG. 5B, an alternative embodiment of integrated pump/oxygenator 80 of the present invention is described. Pump/oxygenator 80 is similar in construction to the device of FIG. 5A, except that fiber bundle assembly 81 includes three sets of symmetric, concentric, fluid impermeable baffles: inner baffles 82 disposed on interior surface 83, middle baffles 84 disposed within the fiber bundle assembly 81, and outer baffles 85 disposed on exterior surface 86. Baffles 82, 84, & 85 extend over predetermined arcs of the circumference of the fiber bundle assembly and for the height of the bundle. Again, the baffles are illustratively spaced equidistant apart from one other within each set, and each set is spaced equidistant apart from the next set. Different spacing and/or number of baffles may be employed. Representative expected flow paths 87 and 88 for blood passing through the fiber bundle assembly are shown in dotted line.

As opposed to the device of FIG. 5A, middle baffles 84 of pump/oxygenator 80 are symmetrically spaced with respect to inner baffles 82 and outer baffles 85. A baffle arrangement of this type is appropriate when the packing density of the porous fibers of bundle assembly 81 is such that symmetric baffles lengthen the blood flow path, illustratively shown by paths 87 and 88.

In FIG. 5C, integrated pump/oxygenator 90 of the present invention is described. Pump/oxygenator 90 is similar in construction to the embodiment of FIGS. 1 and 2 except that, in addition, it includes a plurality of fluid impermeable spiral baffles 92 within fiber bundle 93. Preferably, the hollow fibers used to form fiber bundle 93 are such as are commercially available from, e.g., Hoechst Celanese Corp., Separation Products Division, Charlotte, N.C., and comprise a mat of the longitudinally-aligned tubes woven together with transverse strands. Baffles 92 therefore may be formed by placing potting material at tangentially displaced locations during winding of the mat to form the fiber bundle, for example, as described in the foregoing patent to Prasad et al. The displaced areas of potting material will then harden to form spiral-shaped fluid impermeable vanes.

Unlike the baffles of the embodiments of FIGS. 5A and 5B, the baffles of device 90 include a radial component, and serve to partition fiber bundle 93 into distinct regions. Blood movement through these regions is indicated in dotted line by representative blood flow paths 94 and 95.

Figure 6B:
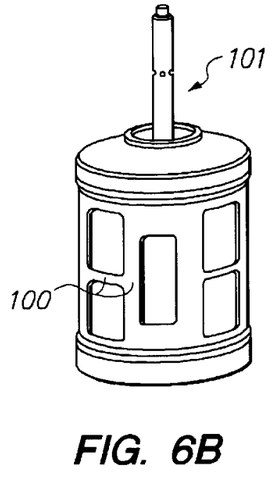
Figure 6C:
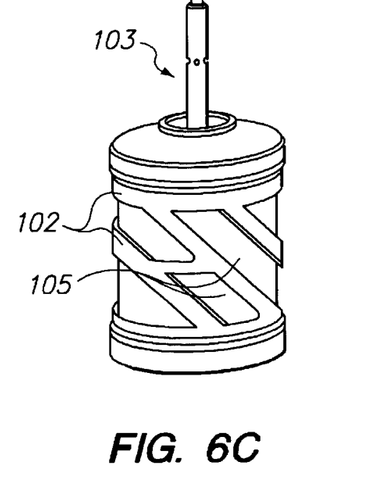

FIGS. 5A–5C describe baffling arrangements that provide two-dimensional increases in flow paths for blood passing through the fiber bundle. Flow path lengthening need not be limited to two dimensions, however, and with a proper choice of baffle patterns, the blood flow paths may be lengthened in three dimensions. FIGS. 6B and 6C depict variations on the types of baffles that may be disposed on or within a fiber bundle assembly of the present invention to enhance the blood flow paths in three dimensions.

Specifically, in FIG. 6B, baffles 100 do not continue over the full height of fiber bundle assembly 101, but instead extend for different lengths along different arcs of the circumference of the fiber bundle. Likewise, in FIG. 6C, baffles 102 of fiber bundle assembly 103 are arranged to form a plurality of windows 105 of different shapes and sizes, thereby enhancing tangential movement of blood within the fiber bundle assembly, and increasing the number of fibers the blood comes in contact with and oxygenation. Other baffle configurations may be incorporated around or within the fiber bundle to promote blood flow through the fiber bundle in the axial direction.

Figure 7:
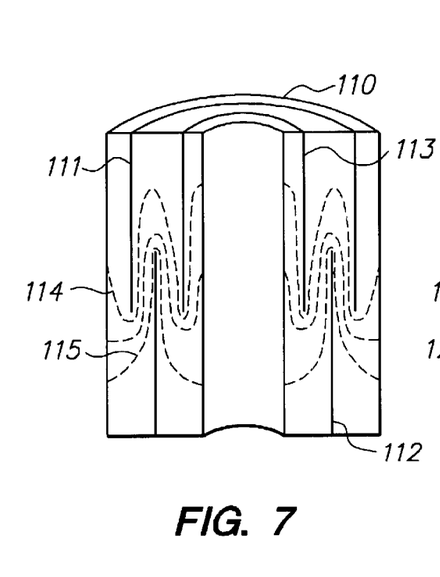
FIG. 7 is a side-sectional views of yet another alternative embodiment of the present invention.

Referring now to FIG. 7, fiber bundle 110 having partial-height baffles disposed within the fiber bundle is described. Fiber bundle 110 is similar to fiber bundle 26 of the device of FIGS. 1 and 2, except that three cylindrical baffles 111, 112 and 113 are disposed within the bundle perpendicular to the radial direction. Each baffle preferably extends over significant length, e.g. two-thirds or more, of the fiber bundle 110. Inner and outer baffles 111 and 113 illustratively are attached to the top of fiber bundle 110, while middle baffle 112 is attached to the bottom of fiber bundle 110. Expected representative blood flow paths 114 and 115 are indicated in dotted line in FIG. 7, showing that the blood travels horizontally and radially on its path through fiber bundle 110. Numerous other blood flow paths are possible by varying the number, shape, size, spacing, location and orientation of the baffles.

Figure 8:
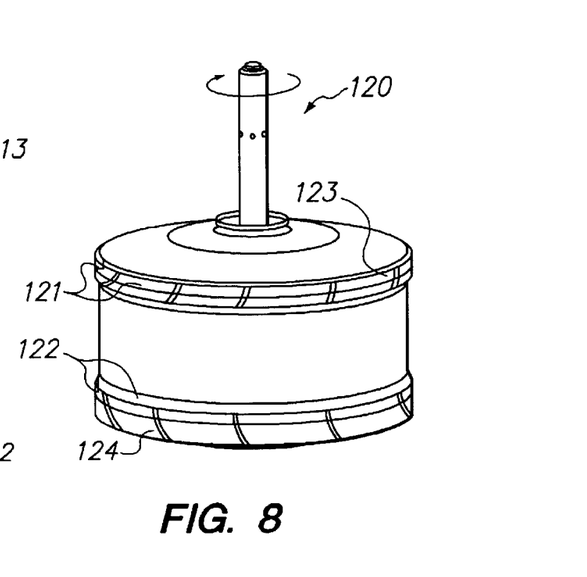
FIG. 8 is a view of a fiber bundle assembly of the present invention having a plurality of recirculating vanes disposed on the gas inlet and gas outlet manifolds.
Figure 9:
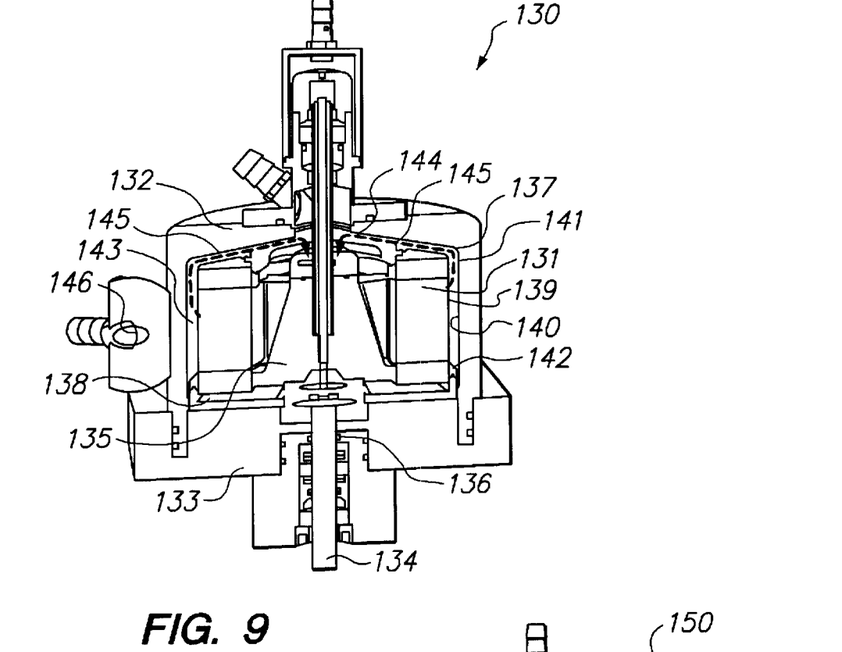
FIG. 9 is a cross-sectional view of a device constructed in accordance with the principles of the present invention that provides internal recirculation paths.
Figure 10:
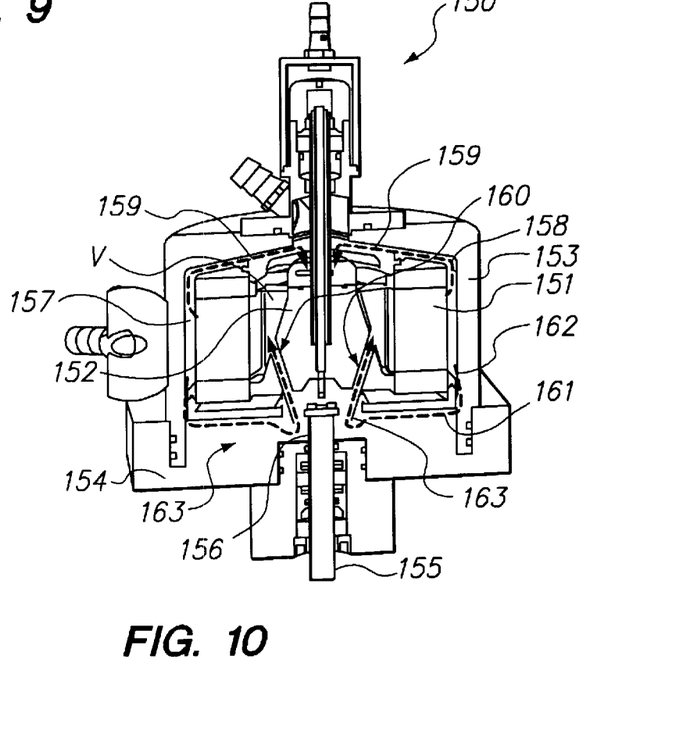
FIG. 10 is a cross-sectional view of an alternative embodiment of the device of FIG. 9.

Referring now to FIGS. 8–10, alternative structures and methods for increasing the path length for blood within the fiber bundle are described. One way this may be accomplished is by recirculating the blood through the fiber bundle before it is returned to the patient, similar to the arrangement described in above-mentioned Hubbard patent. In accordance with the principles of the present invention, recirculation is accomplished by internally recirculating the blood through areas of the integrated pump/oxygenator where the rate of blood flow is comparatively slow. Wash-out from these areas is especially beneficial because, in addition to improving oxygen transfer, it reduces the risk of heat-buildup and hemolysis.

Referring now to FIG. 8, fiber bundle assembly 120 is described. Fiber bundle 120 includes pluralities of vanes 121 and 122 disposed along the outer perimeters of upper and lower gas manifolds 123 and 124, respectively. Vanes 121 and 122 increase the local pressure in the gap between fiber bundle assembly 120 and the interior wall of the device housing (see FIG. 2), thereby enhancing recirculation along the interior wall of the device housing. The number, shape, size, spacing and orientation of vanes 121 and 122 may be determined empirically, while other modifications to pump/oxygenator needed to implement this variation will be apparent to one of ordinary skill in the art of pump design from inspection of FIG. 2.

In FIGS. 9 and 10, alternative embodiments of the integrated pump/oxygenator of the present invention are described wherein the fiber bundle assembly is driven by a drive shaft that may be removably coupled to a motor instead of magnetically coupled. Pump/oxygenator 130 of FIG. 9 includes fiber bundle assembly 131 disposed in housing 132. Housing 132 is fixed to base 133, through which drive shaft 134 is coupled to impeller shaft 135 via suitable rotary seal 136. The gas flow path through fiber bundle assembly 131, including gas manifolds 137 and 138, is similar to that described above with respect to the embodiment of FIGS. 1 and 2.

In accordance with the present invention, annular gap 143 is provided between exterior surface 139 of fiber bundle assembly 131 and interior surface 140 of housing 132. Plurality of vanes 141 is disposed on the perimeter of gas manifold 137 and plurality of vanes 142 is disposed on the perimeter of gas manifold 138, as shown in FIG. 9. The length and pitch of pluralities of vanes 141 and 142 are selected so that a portion of the blood exiting through exterior surface 139 of fiber bundle assembly into annular gap 143 is urged upwards along interior wall 140 of housing 132, through gap 144 between the upper surface of gas manifold 137 and the interior of housing 132, and back into the interior of fiber bundle assembly 131, as indicated by arrows 145.

In this manner, a fraction of the blood passing through pump/oxygenator 130 is recirculated internally within the housing by vanes 141 and 142. Because this recirculated blood is mixed with blood passing through fiber bundle assembly 131 and exiting housing 132 via blood outlet 146, the internal recirculation path provided by pump/oxygenator 130 enhances the oxygen saturation level of blood exiting via blood outlet 146.

Referring to FIG. 10, a further alternative embodiment of the pump/oxygenator of the present invention is provide that includes additional recirculation paths that continuously wash-out blood from regions with heat build-up, thereby further reducing blood trauma. Device 150 is similar in construction to device 130 of FIG. 9, and includes fiber bundle assembly 151 coupled to impeller shaft 152 and disposed for rotation in housing 153. Housing 153 is coupled to base 154 so that fiber bundle assembly 151 is driven by drive shaft 155 that extends through fluid-tight seal 156. The exterior surface of fiber bundle assembly 151 is spaced apart from the interior wall of housing 153 to form annular gap 157.

Plurality of vanes 158 is disposed on the upper manifold to direct blood entering annular gap 157 upwards across the top of the fiber bundle assembly so that it enters void V and is recirculated through the fiber bundle assembly, like the embodiment of FIG. 9, along the path indicated by dotted arrows 159. In addition, impeller shaft 152 includes channels 160 that extend from the surface of impeller shaft 152 in void V to the lower surface of gas manifold 161. Plurality of vanes 162 disposed on the perimeter of gas manifold 161 direct blood from annular gap 157 to flow downwards between gas manifold 161 and base 154, through channels 160, and back into void V along path 163 (indicated by dotted arrows).

Advantageously, channels 160 and vanes 162 of pump/oxygenator 150 cause blood from annular gap 157 to continuously flow through and wash-out blood along the underside of the fiber bundle assembly between gas manifold 161 and the interior surface of base 154. This in turn reduces the risk that blood will stagnate in that region, and therefore also reduce the risk that shear stresses imposed on such blood will result in undue hemolysis or platelet activation. In addition, because blood flowing along path 163 passes through the portion of base 154 through which drive shaft 155 enters the pump/oxygenator, blood flowing along path 163 will tend to dissipate frictional heat build-up between fiber bundle assembly 151 and any supporting thrust surfaces. Consequently, channels 160 and vanes 162 are also expected to reduce blood trauma caused by excessive of pooled blood that may otherwise arise if a wash-out mechanism is not provided.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. An apparatus for processing blood comprising:
    a housing having a gas inlet, a gas outlet, a blood inlet and a blood outlet;
    a shaft disposed within the housing;
    a fiber bundle assembly having an annular bundle of hollow fibers disposed on the shaft for rotation within the housing, the annular bundle having a first end in fluid communication with the gas outlet, and a central void in fluid communication with the blood inlet, rotation of the annular bundle causing blood received within the central void to pass outward through the annular bundle and exit through the blood outlet;
    a plurality of baffles disposed within the fiber bundle assembly, the plurality of baffles re-directing blood flow within the fiber bundle assembly; and
    a plurality of vanes disposed within the central void and affixed to the shaft.

2. The apparatus of claim 1 wherein the plurality of baffles re-directs blood flow along a longitudinal axis of the fiber bundle assembly.

3. The apparatus of claim 2 wherein at least two of the plurality of baffles are disposed at different heights within the fiber bundle assembly.

4. The apparatus of claim 1 wherein the plurality of baffles re-directs blood flow in a transverse direction within the fiber bundle assembly.

5. The apparatus of claim 1 wherein the plurality of baffles are disposed in a circumferential direction relative to the fiber bundle assembly.

6. The apparatus of claim 1 wherein the plurality of baffles are disposed with the fiber bundle assembly in a spiral pattern and partition the fiber bundle assembly into sub-bundles.

7. The apparatus of claim 1 wherein the housing has an interior surface that is spaced apart from an exterior surface of the fiber bundle assembly to form an annular gap, the apparatus further comprising a first plurality of vanes disposed within the annular gap that recirculate blood from the annular gap into the central void.

8. The apparatus of claim 1 further comprising a plurality of pre-accelerating vanes that accelerate blood prior to entry into the central void.

9. The apparatus of claim 1 wherein the shaft includes a plurality of channels that communicate with an underside of the fiber bundle assembly, the apparatus further comprising a plurality of vanes that direct blood along the underside of the fiber bundle assembly and through the channels into the central void.

10. An apparatus for processing blood comprising:
    a housing having a gas inlet, a gas outlet, a blood inlet and a blood outlet;
    a shaft disposed within the housing;
    a fiber bundle assembly having an annular bundle of hollow fibers disposed on the shaft for rotation within the housing, the annular bundle having a first end in fluid communication with the gas outlet, and a central void in fluid communication with the blood inlet, rotation of the annular bundle causing blood received within the central void to pass outward through the annular bundle and exit through the blood outlet;
    a plurality of baffles disposed within the fiber bundle assembly, the plurality of baffles re-directing blood flow within the fiber bundle assembly; and
    a plurality of pre-accelerating vanes that accelerate blood prior to entry into the central void.

11. The apparatus of claim 10, wherein the plurality of baffles re-directs blood flow along a longitudinal axis of the fiber bundle assembly.

12. The apparatus of claim 11, wherein at least two of the plurality of baffles are disposed at different heights within the fiber bundle assembly.

13. The apparatus of claim 10, wherein the plurality of baffles are disposed in a circumferential direction relative to the fiber bundle assembly.

14. The apparatus of claim 10, wherein the plurality of baffles re-directs blood flow in a transverse direction within the fiber bundle assembly.

15. The apparatus of claim 10, wherein the plurality of baffles are disposed with the fiber bundle assembly in a spiral pattern and partition the fiber bundle assembly into sub-bundles.

16. The apparatus of claim 10, wherein the housing has an interior surface that is spaced apart from an exterior surface of the fiber bundle assembly to form an annular gap, the apparatus further comprising a first plurality of vanes disposed within the annular gap that recirculate blood from the annular gap into the central void.

17. The apparatus of claim 10, further comprising a plurality of vanes disposed within the central void and affixed to the shaft.

18. The apparatus of claim 10, wherein the shaft includes a plurality of channels that communicate with an underside of the fiber bundle assembly, the apparatus further comprising a plurality of vanes that direct blood along the underside of the fiber bundle assembly and through the channels into the central void.

19. A method for processing blood comprising:

providing apparatus comprising a housing having a gas inlet and a gas outlet, a blood inlet and a blood outlet, a shaft disposed within the housing, an annular bundle of hollow fibers disposed on the shaft for rotation within the housing and having a first end in fluid communication with the gas inlet, a second end in fluid communication with the gas outlet, and a central void, a plurality of vanes disposed within the central void and affixed to the shaft, and a first plurality of baffles disposed within the annular bundle of hollow fibers;

causing blood to flow into the housing and the central void;

causing a gas comprising oxygen to flow through the hollow fibers of the annular bundle;

rotating the plurality of vanes;

rotating the annular bundle so that blood passes into the annular bundle of hollow fibers; and altering a flow path of blood through the annular bundle of hollow fibers upon the plurality of baffles.

20. The method of claim 19 wherein altering a flow path of blood through the annular bundle of hollow fibers comprises altering a flow path of blood through the annular bundle of hollow fibers in a transverse direction relative to a radius of the annular bundle of hollow fibers.

21. The method of claim 19 wherein altering a flow path of blood through the annular bundle of hollow fibers comprises altering a flow path of blood through the annular bundle of hollow fibers in a longitudinal direction relative to an axis of the annular bundle of hollow fibers.

22. A method for processing blood comprising:

providing apparatus comprising a housing having a gas inlet and a gas outlet, a blood inlet and a blood outlet, a shaft disposed within the housing, an annular bundle of hollow fibers disposed on the shaft for rotation within the housing and having a first end in fluid communication with the gas inlet, a second end in fluid communication with the gas outlet, and a central void, a plurality of pre-accelerating vanes that accelerate blood prior to entry into the central void, and a first plurality of baffles disposed within the annular bundle of hollow fibers;

causing blood to flow into the housing, causing a gas comprising oxygen to flow through the hollow fibers of the annular bundle;

rotating the plurality of pre-accelerating vanes;

causing blood to flow into the central void;

rotating the annular bundle so that blood passes into the annular bundle of hollow fibers; and altering a flow path of blood through the annular bundle of hollow fibers upon the plurality of baffles.

23. The method of claim 22, wherein altering a flow path of blood through the annular bundle of hollow fibers comprises altering a flow path of blood through the annular bundle of hollow fibers in a transverse direction relative to a radius of the annular bundle of hollow fibers.

24. The method of claim 22, wherein altering a flow path of blood through the annular bundle of hollow fibers comprises altering a flow path of blood through the annular bundle of hollow fibers in a longitudinal direction relative to an axis of the annular bundle of hollow fibers.

\* \* \* \* \*